US012758546B2

(12) United States Patent
Jin et al.

(10) Patent No.: US 12,758,546 B2

(45) Date of Patent: Oct. 13, 2026

(54) SUSPENSION OF TRIAZOLE ANTIFUNGAL DRUG FOR ATOMIZER

(71) Applicant: SHANGHAI SHEO PHARMA CO. LTD., Shanghai (CN)

(72) Inventors: Fang Jin, Shanghai (CN); Xiaopei Lian, Shanghai (CN); Cuicui Guo, Shanghai (CN)

(73) Assignee: SHANGHAI SHEO PHARMA CO. LTD., Shanghai (CN)

( * ) Notice: Subject to any disclaimer, the term of this patent is extended or adjusted under 35 U.S.C. 154(b) by 772 days.

(21) Appl. No.: 18/007,476

(22) PCT Filed: Jul. 30, 2021

(86) PCT No.: PCT/CN2021/109420

§ 371 (c)(1),
(2) Date: Jan. 30, 2023

(87) PCT Pub. No.: WO2022/022657

PCT Pub. Date: Feb. 3, 2022

(65) Prior Publication Data

US 2023/0310416 A1 Oct. 5, 2023

(30) Foreign Application Priority Data

Jul. 31, 2020 (CN) ......................... 202010756162.3

(51) Int. Cl.

| | |
|---|---|
| ***A61K 31/496*** | (2006.01) |
| ***A61K 9/00*** | (2006.01) |
| ***A61K 9/10*** | (2006.01) |
| ***A61K 31/4196*** | (2006.01) |
| ***A61K 31/506*** | (2006.01) |
| ***A61K 47/02*** | (2006.01) |
| ***A61K 47/12*** | (2006.01) |
| ***A61K 47/18*** | (2017.01) |
| ***A61K 47/26*** | (2006.01) |

(52) U.S. Cl.

CPC .......... *A61K 31/496* (2013.01); *A61K 9/0078* (2013.01); *A61K 9/10* (2013.01); *A61K 31/4196* (2013.01); *A61K 31/506* (2013.01); *A61K 47/02* (2013.01); *A61K 47/12* (2013.01); *A61K 47/183* (2013.01); *A61K 47/26* (2013.01)

(58) Field of Classification Search

CPC .. A61K 31/496; C07D 249/04; C07D 249/06; C07D 249/08

See application file for complete search history.

(56) References Cited

U.S. PATENT DOCUMENTS

| | | | | |
|---|---|---|---|---|
| 2009/0212021 A1* | 8/2009 | Bernhard | .................. | C23F 1/02<br>252/79.3 |
| 2018/0160679 A1* | 6/2018 | Crozier | .................. | A01N 43/54 |

FOREIGN PATENT DOCUMENTS

| | | | | | |
|---|---|---|---|---|---|
| CN | 101780046 | A | | 7/2010 | |
| CN | 102232929 | A | | 11/2011 | |
| CN | 107281100 | A | | 10/2017 | |
| CN | 111658610 | A | | 9/2020 | |
| EP | 2601973 | A1 | * | 6/2013 | .............. A61P 31/10 |
| JP | 2016037463 | A | * | 3/2016 | |
| WO | WO-2013167865 | A1 | * | 11/2013 | .............. A61P 31/10 |
| WO | WO-2019204583 | A1 | * | 10/2019 | .............. A61P 31/10 |

OTHER PUBLICATIONS

Tween 20. Millipore Sigma Product Page. Published 2024 (Year: 2024).*

Span 20. Millipore Sigma Product Page. Published 2024 (Year: 2024).*

Yuan, et al. "Progress in Research of Preparation Technologies and Drug-Delivery of Nanosuspensions," Chinese Journal of New Drugs, vol. 23 (No. 3), 2014, pp. 297-301, with English translation, 12 pages.

* cited by examiner

*Primary Examiner* — George W Kosturko

(74) *Attorney, Agent, or Firm* — Lewis Roca Rothgerber Christie LLP

(57) ABSTRACT

Provided are a suspension of a triazole antifungal drug for an atomizer, and a preparation method therefor. The pH of the suspension is 3-8. The suspension comprises a triazole antifungal drug, a surfactant, an osmotic pressure regulator, a metal complexing agent, a pH regulator and water, wherein the triazole antifungal drug has a D50 diameter of 1-10 μm, and accounts for 0.025%-1% of the total mass of the suspension, and the mass ratio of the triazole antifungal drug to the surfactant is 1:1-50:1.

15 Claims, 2 Drawing Sheets

SUSPENSION OF TRIAZOLE ANTIFUNGAL DRUG FOR ATOMIZER

CROSS-REFERENCE TO RELATED APPLICATIONS

The present application is a U.S. National Phase Patent Application of International Application Number PCT/CN2021/109420, filed on Jul. 30, 2021, which claims the benefit of priority to Chinese Patent Application No. 202010756162.3 filed on Jul. 31, 2020, the entire contents of each of which are incorporated herein by reference.

FIELD OF THE INVENTION

The present invention belongs to the field of pharmaceutical preparations, particularly relates to a liquid preparation for atomizer.

BACKGROUND ART

With the increase of immunosuppressive population, the incidence rate of fungal infection has shown a remarkable rising trend. The fungal infection is mostly caused by inhaling fungal spores through respiratory tract, and the lung is the high-incidence site of an invasive fungal infection, therefore the maintain of high drug concentration in lung tissue and the inhibition of propagation of the spores in the lung become the key to preventive and targeted antifungal treatment. In order to maintain the high concentration in lung tissue, the dosage of antifungal drugs must be increased when they are applied through conventional routes (such as intravenous drip/oral administration), but at the same time, the adverse reactions are significantly increased. Compared with the conventional modes of administration, aerosol inhalation can achieve higher drug concentration in the lung, control fungal infection and colonization, and avoid various adverse reactions caused by systemic administration at the same time. Therefore, there has been an increase in the study of antifungal drugs by aerosol inhalation since the 1990s. Since triazole antifungal drugs are more easily absorbed into the blood through respiratory tract than amphotericin, liquid preparations of triazole antifungal drugs for atomizers has attracted the interest of pharmaceutical companies and research institutions.

When developing a suspension of triazole antifungal drugs for atomizer, the inventor found that if the proportion of surfactant used in the inhaled liquid preparation on the market was prepared according to the specifications of this product, the prepared suspension had poor stability, and drug particles would obviously agglomerate after being placed at room temperature for 3 months, so that such suspension was not suitable for medical use.

SUMMARY OF THE INVENTION

In order to solve the above-mentioned technical problems, the present invention provides a suspension of triazole antifungal drugs for atomizer. The suspension of the present invention can be stable at room temperature for 1 year, the particle size does not increase obviously, and the suspension of the present invention meets the requirements for medical use.

In order to achieve the above purpose, the present invention adopts the following technical solutions:

A suspension of triazole antifungal drugs for atomizer, with a pH of 3~8, comprising a triazole antifungal drug, a surfactant, an osmotic pressure regulator, a metal complexing agent, a pH regulator and water; wherein the triazole antifungal drug has a D50 of 1~10 μm, the amount of the triazole antifungal drug is 0.025%~1% based on the total mass of the suspension, and the mass ratio of the triazole antifungal drug to the surfactant is 1:1~50:1.

Preferably, the triazole antifungal drug has a D50 of 1.5~5.5 μm.

Preferably, the amount of the triazole antifungal drug is 0.25%~0.5% based on the total mass of the suspension.

Preferably, the mass ratio of the triazole antifungal drug to the surfactant is 1:1 20:1.

Preferably, the triazole antifungal drug is one selected from the group consisting of ketoconazole, itraconazole, sapiconazole, fluconazole and voriconazole, or one selected from pharmaceutically acceptable salts thereof.

Preferably, the surfactant is one or more selected from the group consisting of non-ionic surfactants and amphoteric surfactants.

Preferably, the non-ionic surfactant is selected from one or more selected from the group consisting of Span 20 (dehydrated sorbitol monolaurate), Tween 20(polyoxyethylene dehydrated sorbitol monolaurate), Tween 80 (polyoxyethylene dehydrated sorbitol monooleate), polysorbates, polyoxyethylene castor oil, poloxamer, glycerol, polyethylene glycol 400, oleyl polyoxyethylene (2) ether, stearyl polyoxyethylene (2) ether, lauryl polyoxyethylene (4) ether, ethylene oxide and propylene oxide block copolymers, diethylene glycol dioleate, tetrahydrofurfuryl oleate, ethyl oleate, glycerol monooleate and glycerol monolaurate.

Preferably, the amphoteric surfactant is one or more selected from the group consisting of natural lecithin, synthetic lecithin and phospholipids.

More preferably, the surfactant is one or more selected from the group consisting of Span 20, Tween 80 and Span 20.

Further preferably, the surfactant is a mixture of Tween 80 and Span 20, and the mass ratio of Tween 80 to Span 20 is 5:1~100:1.

Most preferably, the surfactant is a mixture of Tween 80 and Span 20, and the mass ratio of Tween 80 to Span 20 is 20:1~40:1.

Preferably, the suspension has a pH of 5~7.

Preferably, the pH regulator is a conventional reagent or pH buffer in the art for adjusting or maintaining the pH value of liquid medicine.

Further preferably, the pH regulator is selected from the group consisting of citric acid, hydrochloric acid, sodium hydroxide and pH buffer.

The pH buffer is one selected from the group consisting of citric acid-sodium citrate, acetic acid-sodium acetate and sodium dihydrogen phosphate-disodium hydrogen phosphate.

Preferably, the amount of the osmotic pressure regulator is 0.7%~1.0% based on the total mass of the suspension.

More preferably, the amount of the osmotic pressure regulator is 0.8%~0.9% based on the total mass of the suspension.

Preferably, the osmotic pressure regulator is one selected from the group consisting of sodium chloride, potassium chloride, glucose, mannitol, xylitol and lactose.

Preferably, the amount of the metal complexing agent is 0%~0.1% based on the total mass of the suspension.

More preferably, the amount of the metal complexing agent is 0.01%~0.05% based on the total mass of the suspension.

Preferably, the metal complexing agent is one or more in any proportion selected from edetic acid and salts thereof.

As a preferred embodiment, the present invention provides a suspension of triazole antifungal drugs for atomizer, with a pH of 3~8, comprising a triazole antifungal drug, a surfactant, an osmotic pressure regulator, a metal complexing agent, a pH regulator and water; wherein the triazole antifungal drug has a D50 of 1~10 μm, the mass ratio of the triazole antifungal drug to the surfactant is 1:1 50:1; the amount of the triazole antifungal drug is 0.025%~1%, the amount of the osmotic pressure regulator is 0.7~1.0%, the amount of the metal complexing agent is 0%~0.1% based on the total mass of the suspension.

As a more preferred embodiment, the present invention provides a suspension of triazole antifungal drugs for atomizer, with a pH of 5~7, and comprising a triazole antifungal drug, a surfactant, an osmotic pressure regulator, a metal complexing agent, a pH regulator and water; wherein the triazole antifungal drug has a D50 of 1.5~5.5 μm, the mass ratio of the triazole antifungal drug to the surfactant is 1:1~20:1; the amount of the triazole antifungal drug is 0.025%~0.5%, the amount of the osmotic pressure regulator is 0.8~0.9%, the amount of the metal complexing agent is 0.01%~0.05% based on the total mass of the suspension.

In the above-mentioned preferred embodiments, the triazole antifungal agent, the surfactant, the osmotic pressure regulator, the metal complexing agent and the pH regulator are as defined above.

Another objective of the present invention is to provide a method for preparing the suspension of triazole antifungal drugs for atomizer above comprising the following steps:

(1) preparing each component according to the prescription;
(2) dissolving the surfactant with 90%±5% of the prescribed amount of water;
(3) adding the remaining excipients including the osmotic pressure regulator, the metal complexing agent and the pH regulator, and stirring to dissolve completely;
(4) adding water to the specified weight, stirring to mix uniformly, and measuring the pH value to obtain a excipient solution;
(5) filtering the excipient solution to remove bacteria;
(6) adding a prescription amount of sterile triazole antifungal drugs in powder form, and stirring or homogenizing to disperse the triazole antifungal drugs uniformly; and
(7) filling quantitatively in ampoules, and sealing.

Unless otherwise specified, the term “water” as used herein, refers to the water treated to be suitable for a liquid preparation for atomizer, which includes water for injection, redistilled water and the like.

After being placed at room temperature for 1 year, the particle size of the suspension of triazole antifungal drugs for atomizer provided by the present invention only slightly increases, or even does not increase, which meets the requirements for medical use.

BRIEF DESCRIPTION OF THE FIGURES

The present invention will be further described with reference to the Figures.

DETAILED DESCRIPTION OF THE INVENTION

Figure 1:
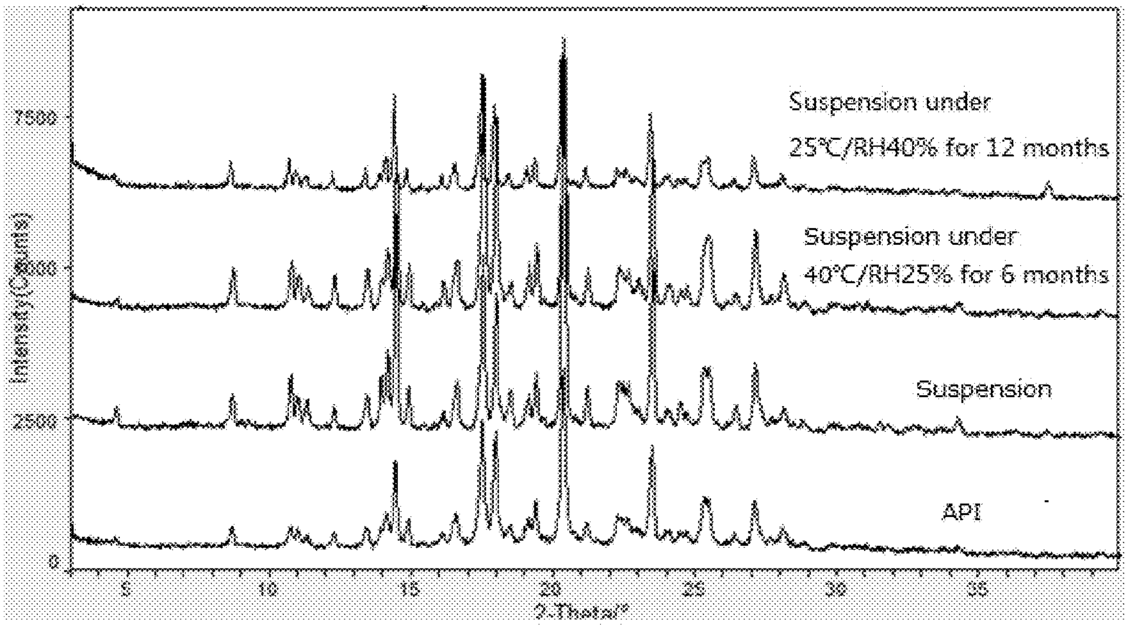
FIG. 1 shows the comparison of the X-ray diffraction patterns of the drug crystal form of the suspension in Example 2 under the conditions of 25° C.±2° C./RH 40%±5% for 12 months and 40° C.±2° C./not more than RH25% for 6 months respectively; wherein from top to bottom, they are the X-ray diffraction pattern of the crystal form of the suspension under the condition of 25° C.±2° C./RH40%±5% for 12 months, the suspension under the condition of 40° C.±2° C./not more than RH25% for 6 months, a freshly prepared preparation and the active pharmaceutical ingredient (API) respectively.

The present invention is illustrated below with reference to specific examples. It will be understood by those skilled in the art that these examples are merely illustrative of the present invention and do not limit the scope of the present invention in any way.

The experimental methods in the following examples are all conventional methods unless otherwise specified. The raw materials, reagent materials and the like used in the following examples are all commercially available products unless otherwise specified.

Example 1: 100 kg Itraconazole Suspension for Atomizer (1) about 90 kg of water for injection was added into a preparation tank, then added with 500 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;
(3) water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 2: 100 kg Itraconazole Suspension for Atomizer (1) about 90 kg of water for injection was added into a preparation tank, then added with 100 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;

(3) Water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 3: 100 kg Itraconazole Suspension for Atomizer (1) about 90 kg of water for injection was added into a preparation tank, then added with 25 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;
(3) water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 4: 100 kg Itraconazole Suspension for Atomizer (1) about 90 kg of water for injection was added into a preparation tank, then added with 12.5 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;
(3) water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 5: 100 kg Itraconazole Suspension for Atomizer (1) about 90 kg of water for injection was added into a preparation tank, then added with 10 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;
(3) water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 6: 100 kg Itraconazole Suspension for Atomizer (1) about 90 kg of water for injection was added into a preparation tank, then added with 8.3 g of Tween 80, and stirred to dissolve completely;
(2) 800 g of sodium chloride, 10 g of edetate disodium, 180 g of disodium hydrogen phosphate and 940 g of sodium dihydrogen phosphate were added thereinto, and stirred to dissolve completely;
(3) water for injection was added up to 99.5 kg, stirred to mix uniformly, the pH value was 6.0, an excipient solution was obtained;
(4) the excipient solution was filtered through a 0.2 μm sterilization filter, then transferred to a sterile storage tank;
(5) 500 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 7: 100 kg Itraconazole Suspension for Atomizer (1) about 90 kg of water for injection was added into a preparation tank, then added with 25 g of Tween 80, and stirred to dissolve completely;
(2) 850 g of sodium chloride, 20 g of edetate disodium, 27 g of citrate monohydrate and 330 g of trisodium citrate dihydrate were added thereinto, and stirred to dissolve completely;
(3) water for injection was added up to 98.8 kg, stirred to mix uniformly, the pH value was 6.0, an excipient solution was obtained;
(4) the excipient solution was filtered through a 0.2 μm sterilization filter, then transferred to a sterile storage tank;
(5) 1200 g of sterile itraconazole as API was added into the excipient solution which were filtered to remove bacteria under the condition of Class A laminar flow protection; stirred or homogenize to disperse itraconazole uniformly;
(6) filled under sterilization and sealed.

Example 8: 100 kg Itraconazole Suspension for Atomizer (1) about 90 kg of water for injection was added into a preparation tank, then added with 10.4 g of Tween 80 and 2.1 g of Span 20, and stirred to dissolve completely;

(2) 800 g of sodium chloride, 10 g of edetate disodium, 180 g of disodium hydrogen phosphate and 940 g of sodium dihydrogen phosphate were added thereinto, and stirred to dissolve completely;

(3) water for injection was added up to 99.5 kg, stirred to mix uniformly, the pH value was 6.0, an excipient solution was obtained;

(4) the excipient solution was filtered through a 0.2 μm sterilization filter, then transferred to a sterile storage tank;

(5) 500 g of sterile itraconazole as API was added into the excipient solution which were filtered to remove bacteria under the condition of Class A laminar flow protection; stirred or homogenize to disperse itraconazole uniformly;

(6) filled under sterilization and sealed.

Example 9: 100 kg Itraconazole Suspension for Atomizer (1) about 90 kg of water for injection was added into a preparation tank, then added with 12.19 g of Tween 80 and 0.31 g of Span 20, and stirred to dissolve completely;

(2) 800 g of sodium chloride, 10 g of edetate disodium, 180 g of disodium hydrogen phosphate and 940 g of sodium dihydrogen phosphate were added thereinto, and stirred to dissolve completely;

(3) water for injection was added up to 99.5 kg, stirred to mix uniformly, the pH value was 6.0, an excipient solution was obtained;

(4) the excipient solution was filtered through a 0.2 μm sterilization filter, then transferred to a sterile storage tank;

(5) 500 g of sterile itraconazole as API was added into the excipient solution which were filtered to remove bacteria under the condition of Class A laminar flow protection; stirred or homogenize to disperse itraconazole uniformly;

(6) filled under sterilization and sealed.

Example 10: 100 kg Itraconazole Suspension for Atomizer (1) about 90 kg of water for injection was added into a preparation tank, then added with 12.3 g of Tween 80 and 0.2 g of Span 20, and stirred to dissolve completely;

(2) 800 g of sodium chloride, 10 g of edetate disodium, 180 g of disodium hydrogen phosphate and 940 g of sodium dihydrogen phosphate were added thereinto, and stirred to dissolve completely;

(3) water for injection was added up to 99.5 kg, stirred to mix uniformly, the pH value was 6.0, an excipient solution was obtained;

(4) the excipient solution was filtered through a 0.2 μm sterilization filter, then transferred to a sterile storage tank;

(5) 500 g of sterile itraconazole as API was added into the excipient solution which were filtered to remove bacteria under the condition of Class A laminar flow protection; stirred or homogenize to disperse itraconazole uniformly;

(6) filled under sterilization and sealed.

Example 11: 100 kg Itraconazole Suspension for Atomizer (1) about 90 kg of water for injection was added into a preparation tank, then added with 12.38 g of Tween 80 and 0.12 g of Span 20, and stirred to dissolve completely;

(2) 800 g of sodium chloride, 10 g of edetate disodium, 180 g of disodium hydrogen phosphate and 940 g of sodium dihydrogen phosphate were added thereinto, and stirred to dissolve completely;

(3) Water for injection was added up to 99.5 kg, stirred to mix uniformly, the pH value was 6.0, an excipient solution was obtained;

(4) the excipient solution was filtered through a 0.2 μm sterilization filter, then transferred to a sterile storage tank;

(5) 500 g of sterile itraconazole as API was added into the excipient solution which were filtered to remove bacteria under the condition of Class A laminar flow protection; stirred or homogenize to disperse itraconazole uniformly;

(6) filled under sterilization and sealed.

Example 12: 100 kg Ketoconazole Suspension for Atomizer (1) about 90 kg of water for injection was added into a preparation tank, then added with 50 g of Tween 80, and stirred to dissolve completely;

(2) 850 g of sodium chloride, 5 g of edetate disodium were added thereinto, and stirred to dissolve completely;

(3) dilute hydrochloric acid was added to adjust the pH value, water for injection was added up to 99.5 kg, stirred to mix uniformly, the pH value was 5.5, an excipient solution was obtained;

(4) the excipient solution was filtered through a 0.2 μm sterilization filter, then transferred to a sterile storage tank;

(5) 500 g of sterile ketoconazole as API was added into the excipient solution which were filtered to remove bacteria under the condition of Class A laminar flow protection; stirred or homogenize to disperse itraconazole uniformly;

(6) filled under sterilization and sealed.

Example 13: 100 kg Voriconazole Suspension for Atomizer (1) about 90 kg of water for injection was added into a preparation tank, then added with 2 g of dipalmitoyl lecithin, and stirred to dissolve completely;

(2) 850 g of sodium chloride, 15 g of edetate disodium, 27 g of citrate monohydrate and 330 g of trisodium citrate dihydrate were added thereinto, and stirred to dissolve completely;

(3) water for injection was added up to 100 kg, stirred to mix uniformly, the pH value was 6.0, an excipient solution was obtained;

(4) the excipient solution was filtered through a 0.2 μm sterilization filter, then transferred to a sterile storage tank;

(5) 50 g of sterile voriconazole as API was added into the excipient solution which were filtered to remove bacteria under the condition of Class A laminar flow protection; stirred or homogenize to disperse itraconazole uniformly;

(6) filled under sterilization and sealed.

Example 14: 100 kg Fluconazole Suspension for Atomizer (1) about 90 kg of water for injection was added into a preparation tank, then added with 25 g of Tween 80, and stirred to dissolve completely;
(2) 800 g of sodium chloride, 130 g of citrate monohydrate and 1000 g of trisodium citrate dihydrate were added thereinto, and stirred to dissolve completely;
(3) water for injection was added up to 99.5 kg, stirred to mix uniformly, the pH value was 5.0, an excipient solution was obtained;
(4) the excipient solution was filtered through a 0.2 μm sterilization filter, then transferred to a sterile storage tank;

(5) 500 g of sterile fluconazole as API was added into the excipient solution which were filtered to remove bacteria under the condition of Class A laminar flow protection; stirred or homogenize to disperse itraconazole uniformly;
(6) filled under sterilization and sealed.

Detection Example

The suspensions freshly prepared in Examples 1 to 14 were all white suspensions, well dispersed and the average particle size is about 2.2 μm (the particle size was determined by utilizing an HELOS/BR-multi laser particle sizer (SUCELL module, SYMPATEC GmbH, Germany)).

1. Stability Study

The suspensions prepared in Examples 1 to 14 were investigated under the condition of 25° C.±2° C./RH40%±5% for 12 months and under the condition of 40° C.±2° C./not more than RH25% for 6 months, respectively.

After being taken out, the sample appearance and the shaking dispersion were observed, and the particle size was detected. The results are shown in Table 1.

TABLE 1

Stability results of samples from all examples

| | | | | 25° C. + 2° C./RH40% + 5% for 12 months | | 40° C. + 2° C./not more than RH25% for 6 months | |
|---|---|---|---|---|---|---|---|
| Preparation | Surfactant | API/ Surfactant | Tween 80/ Span 20 | Uniformity of dispersion | Average particle diameter | Uniformity of dispersion | Average particle diameter |
| Example 1 | Tween 80 | 1:1 | | White suspension, well dispersed, without agglomeration | 2.20 μm | White suspension, dispersed well, no agglomeration | 2.43 μm |
| Example 2 | Span 80 | 5:1 | | White suspension, well dispersed, without agglomeration | 2.15 μm | White suspension, dispersed well, no agglomeration | 2.39 μm |
| Example 3 | Tween 80 | 20:1 | | White suspension, well dispersed, without agglomeration | 2.23 μm | White suspension, dispersed well, no agglomeration | 2.50 μm |
| Example 4 | Tween 80 | 40:1 | | White suspension, well dispersed, without agglomeration | 3.12 μm | White suspension, dispersed well, no agglomeration | 3.53 μm |
| Example 5 | Tween 80 | 50:1 | | White suspension, well dispersed, without agglomeration | 3.57 μm | White suspension, dispersed well, no agglomeration | 3.95 μm |
| Example 6 | Tween 80 | 60.2:1 | | White suspension, slightly adhered on the bottle wall | N/A | agglomerated drug particles | N/A |
| Example 7 | Tween 80 | 48:1 | | White suspension, slightly adhered on the bottle wall | N/A | Agglomerated drug particles | N/A |
| Example 8 | Tween 80, Span 20 | 40:1 | 4.95:1 | White suspension, well dispersed, without agglomeration | 2.87 μm | White suspension, dispersed well, no agglomeration | 3.04 μm |
| Example 9 | Tween 80, Span 20 | 40:1 | 39.3:1 | White suspension, well dispersed, without agglomeration | 2.32 μm | White suspension, dispersed well, no agglomeration | 2.57 mu m |
| Example 10 | Tween 80, Span 20 | 40:1 | 61.5:1 | White suspension, well dispersed, without agglomeration | 2.94 μm | White suspension, dispersed well, no agglomeration | 3.15 μm |
| Example 11 | Tween 80, Span 20 | 40:1 | 103.2:1 | White suspension, well dispersed, without agglomeration | 3.35 μm | White suspension, dispersed well, no agglomeration | 3.76 μm |

TABLE 1-continued

Stability results of samples from all examples

| Preparation | Surfactant | API/ Surfactant | Tween 80/ Span 20 | 25° C. + 2° C./RH40% + 5% for 12 months: Uniformity of dispersion | 25° C. + 2° C./RH40% + 5% for 12 months: Average particle diameter | 40° C. + 2° C./not more than RH25% for 6 months: Uniformity of dispersion | 40° C. + 2° C./not more than RH25% for 6 months: Average particle diameter |
|---|---|---|---|---|---|---|---|
| Example 12 | Tween 80 | 10:1 | | White suspension, well dispersed, without agglomeration | 3.01 μm | White suspension, dispersed well, no agglomeration | 3.40 μm |
| Example 13 | Dipalmitoyl lecithin | 25:1 | | White suspension, well dispersed, without agglomeration | 3.04 μm | White suspension, dispersed well, no agglomeration | 3.33 μm |
| Example 14 | Tween 80 | 20:1 | | White suspension, well dispersed, without agglomeration | 3.07 μm | White suspension, dispersed well, no agglomeration | 3.45 mu m |

2. Investigation of Crystal Form During the Stability Study

The suspensions freshly prepared, under the condition of 25° C.±2° C./RH 40%±5% for 12 months and under the condition of 40° C.±2° C./not more than RH25% for 6 months in Example 2 were sampled respectively and suction filtered through a 0.45 μm filter membrane to obtain the solid components (mainly itraconazole) in the suspension. The solid components were washed with pure water (to remove excipients attached to the surface of the APIs), dried in vacuum, and the collected samples were detected by X-ray powder diffraction. The X-ray diffraction pattern of each sample is shown in FIG. 1.

FIG. 1 shows that the crystal form of the API used in the production of the present preparation has not changed and no new crystal form has been generated after being prepared into a preparation through a determined preparation process. During the stability study, for example, under the condition of 40° C.±2° C./not more than RH25% for 6 months and under the condition of 25° C.±2° C./RH40%±5% for 12 months, the crystalline form has not unchanged and no new crystalline form has been generated, indicating that the suspension prepared by the present invention is stable, and there is no crystalline form change problem during the stability study.

3. Investigation of Drug Dispersion State During the Stability Study

Figure 2:
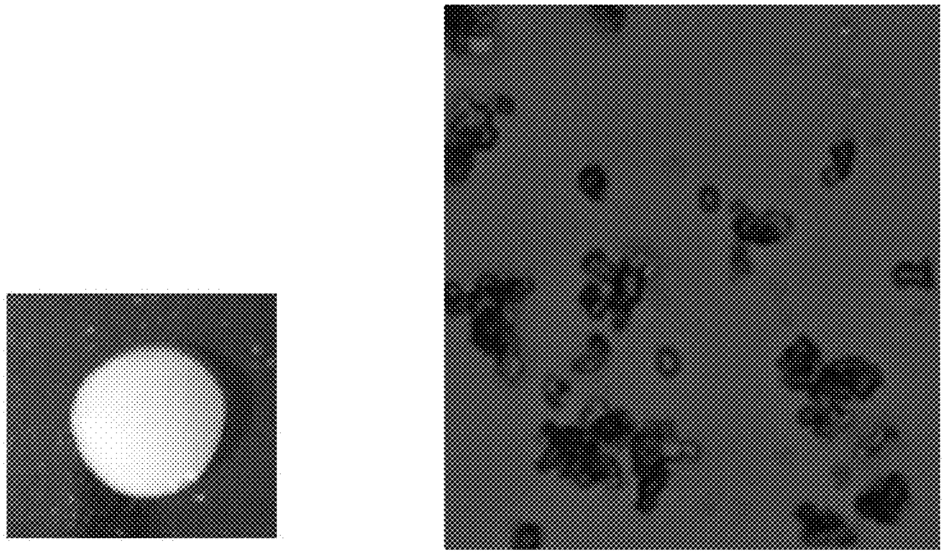
FIG. 2 shows photographs of the API of the freshly prepared preparation in Example 6 in the dispersion state, wherein the left panel shows the phenomenon observed by the naked eyes when the suspension is dropped onto the slide, and the right panel shows the photograph magnified 1000 times by a polarized microscope.
Figure 3:
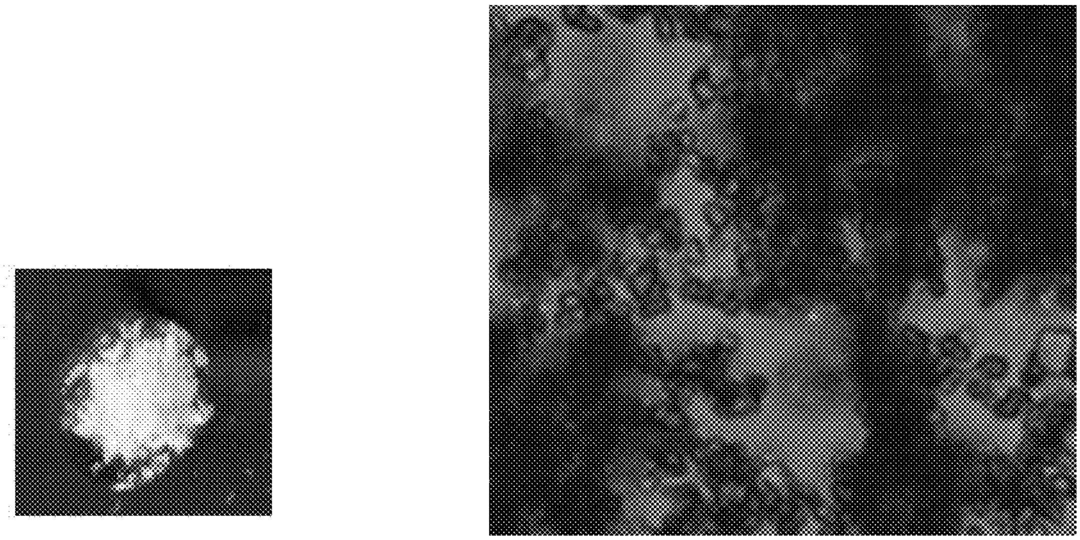
FIG. 3 shows photographs of the API of the preparation in Example 6 after 3 months under the condition of 25° C.±2° C./RH 40%±5%; wherein the left panel shows the phenomenon observed by the naked eyes when the suspension is dropped onto the slide, and the right panel shows the photograph magnified 1000 times by a polarized microscope.

The suspensions freshly prepared and under the condition of 25° C.±2° C./RH40%±5% for 3 months were sampled respectively, and dropped on a slide for observation (please see left panels of FIGS. 2 and 3, respectively): the API in the freshly prepared suspension was well dispersed, while the API agglomerated in the sample for the stability study and can not be dispersed after shaking. Then, a polarized microscope (LV100N POL type, Nikon) was used to observe under 1000 times magnification (see the right panels of FIG. 2 and FIG. 3 respectively): the API in the freshly prepared suspension was well dispersed, while the API agglomerated in the sample for the stability study. When the mass ratio of the API to the surfactant was 60:1, the suspension was unstable and did not meet the requirements for medical use.

Experimental Example on Efficacy

In order to investigate the efficacy of itraconazole suspension of the present invention by inhalation administration, a mouse model of pulmonary fibrosis induced by bleomycin 2 mg/kg/mouse was established and compared with that by oral administration.

Test animals: ICR mice: SPF grade, body weight 22-24 g, male.

Test drugs: itraconazole suspension prepared in Example 3

Instruments and equipment:

| Names of Instruments | Types | Manufacturers |
|---|---|---|
| Electronic analytical balance | AG245 | Mettler TOLEDO |
| Compression atomizer | SX | PARI BOY ® |
| Water purifier | MicroPure | Thermo |
| Microplate Reader | xMark | Bio-Rad |
| Cryogenic centrifuge | fresco | SORVALL ® |
| Microscope | BX51 | OLYMPUS |
| Embedding machine | EG1150H | LEICA |
| Slicing machine | RM2235 | LEICA |
| Cooling table | EG1150C | LEICA |
| Film spreader | HI1210 | LEICA |
| Pipette | Research | Eppendorf |
| High performance liquid chromatography(HPLC) | LC-10AD vp | Shimadzu |

Model establishment: 2 mg/kg of bleomycin hydrochloride for injection was sprayed into the respiratory tract of each mouse to induce pulmonary fibrosis, 4 weeks later, a mouse pulmonary fibrosis model was established.

Animal grouping: Mice were randomly divided into 4 groups, namely a blank control group, a model group, an itraconazole inhalation group, in which 2.5 mg/kg was inhaled for 3 minutes (2.5 mg/kg Inhalation group) and an itraconazole oral group, in which 15 mg/kg was orally administrated(15 mg/kg Oral group). The drugs were administered once a day for 22 consecutive days from the fifth day after modeling.

Detecting indexes: the mice were sacrificed after administration, the trachea was separated, the left lung was ligated, the bronchoalveolar lavage (BAL) was performed, the bronchoalveolar lavage fluid (BALF) was taken for white cell count and classification count, after the lung tissue was fixed with formalin, paraffin embedding, sectioning, H & E staining and Masson's staining were carried out. The contents of transforming growth factor (TGF-β(1), mouse type I collagen (Col I) and hydroxyproline in lung tissue in supernatant of the BALF were detected by a kit. The results are shown in a Table 2.

The results showed that the 2.5 mg/kg Inhalation group can obviously reduce inflammatory cells infiltration and collagen formation in lung tissue, and decrease the contents of TGF-β1 and Col I in BALF and the content of hydroxyproline in lung tissue. Though the dose of itraconazole by inhalation administration (2.5 mg/kg) was only ⅙ times of that by oral administration (15 mg/kg), the effect on the model was much stronger, indicating that the efficacy of itraconazole by inhalation administration is obviously better than that by oral administration.

the amphoteric surfactant is one or more selected from the group consisting of natural lecithin, synthetic lecithin and phospholipids:

wherein an amount of the osmotic pressure regulator is 0.7%~1.0% based on the total mass of the suspension; and wherein an amount of the metal complexing agent is 0.01%~0.05% based on the total mass of the suspension.

TABLE 2

Effects of itraconazole by different routes of administration on bleomycin-induced idiopathic pulmonary fibrosis in mice

| Indexes | Control groups | Model groups | 2.5 mg/kg Inhalation group | 15 mg/kg Oral group |
|---|---|---|---|---|
| Total number of white blood cells in BALF (1 ×10 $^{4}$ cell/ml) | 4.5 ± 1.25 | 32.56 ± 10.09 | 26.13 ± 5.93 | 29.13 ± 10.99 |
| Number of neutrophils in BALF (1 ×10 $^{4}$ cell/ml) | 0.28 ± 0.09 | 20.99 ± 9.69 | 12.08 ± 5.85 | 13.71 ± 7.58 |
| Content of TGF-β1 in BALF(pg/ml) | 18.44 ± 0.59 | 51.16 ± 15.08 | 32.13 ± 25.97 | 24.79 ± 12.72 |
| Content of Col I in BALF (ng/ml) | 0.26 ± 0.23 | 2.1 ± 1.17 | 1.64 ± 0.64 | 1.91 ± 0.86 |
| Content of hydroxyproline in lung tissue (μg/g tissue) | 469.2 ± 74.5 | 608.9 ± 61.1 | 526.7 ± 66.0 | 583.8 ± 96.6 |
| Collagen deposition in lung tissue | 28661.7 ± 5408.9 | 204340.7 ± 37058.4 | 62759.9 ± 17865.8 | 166628.8 ± 35819.8 |

The results showed that 2.5 mg/kg Inhalation group can obviously reduce inflammatory cell infiltration and collagen formation in lung tissue, and decrease the contents of TGF-β1 and Col I in BALF and the content of hydroxyproline in lung tissue. Though the dose of itraconazole by inhalation administration (2.5 mg/kg) was only ⅙ times of that by oral administration (15 mg/kg), the effect on the model was much stronger, indicating that the efficacy of itraconazole by inhalation administration is obviously better than that by oral administration.

The invention claimed is:

1. A suspension of triazole antifungal drug for atomizer, with a pH value of 3~8, comprising a triazole antifungal drug, a surfactant, an osmotic pressure regulator, a metal complexing agent, a pH regulator and water;

wherein the triazole antifungal drug has a D50 of 1~10 μm, an amount of the triazole antifungal drug is 0.025%~1% based on a total mass of the suspension, and a mass ratio of the triazole antifungal drug to the surfactant is 1:1~50:1;

wherein the surfactant is one or more selected from the group consisting of non-ionic surfactants and amphoteric surfactants, the non-ionic surfactant is one or more selected from the group consisting of dehydrated sorbitol monolaurate, polyoxyethylene dehydrated sorbitol monolaurate, polyoxyethylene dehydrated sorbitol monooleate, polysorbates, polyoxyethylene castor oil, poloxamer, glycerol, polyethylene glycol 400, oleyl polyoxyethylene (2) ether, stearyl polyoxyethylene (2) ether, lauryl polyoxyethylene (4) ether, ethylene oxide and propylene oxide block copolymers, diethylene glycol dioleate, tetrahydrofurfuryl oleate, ethyl oleate, glycerol monooleate and glycerol monolaurate, and

2. The suspension according to claim 1, wherein the triazole antifungal drug has a D50 of 1.5~5.5 μm.

3. The suspension according to claim 1, wherein the amount of the triazole antifungal drug is 0.25%~0.5% based on the total mass of the suspension.

4. The suspension according to claim 1, wherein the mass ratio of the triazole antifungal drug to the surfactant is 1:1~20:1.

5. The suspension according to claim 1, wherein the triazole antifungal drug is one selected from the group consisting of ketoconazole, itraconazole, sapiconazole, fluconazole and voriconazole, or a pharmaceutically acceptable salt thereof.

6. The suspension according to claim 1, wherein the surfactant is a mixture of polyoxyethylene dehydrated sorbitol monooleate and dehydrated sorbitol monolaurate, and a mass ratio of polyoxyethylene dehydrated sorbitol monooleate to dehydrated sorbitol monolaurate is 5:1~100:1.

7. The suspension according to claim 1, wherein the suspension has a pH value of 5~7.

8. The suspension according to claim 1, wherein the amount of the osmotic pressure regulator is 0.8%~0.9% based on the total mass of the suspension.

9. The suspension of claim 1, wherein the metal complexing agent is one or more selected from edetic acid and salts thereof.

10. A method for preparing the suspension of triazole antifungal drug for atomizer according to claim 1 comprising the following steps:

(1) preparing each component according to the prescription;

(2) dissolving the surfactant with 90%±5% of the prescribed amount of water;

(3) adding the remaining excipients including the osmotic pressure regulator, the metal complexing agent and the pH regulator, and stirring to dissolve completely;

(4) adding water to the specified weight, stirring to mix uniformly, and measuring the pH value to obtain an excipient solution;

(5) filtering the excipient solution to remove bacteria;

(6) adding a prescription amount of sterile triazole antifungal drug in powder form, and stirring or homogenizing to disperse the triazole antifungal drug uniformly;

(7) filling quantitatively in ampoules, and sealing.

11. The suspension of claim 6, wherein the mass ratio of polyoxyethylene dehydrated sorbitol monooleate to dehydrated sorbitol monolaurate is 20:1~40:1.

12. The suspension of claim 1, wherein the pH regulator is a conventional reagent or pH buffer in the art for adjusting or maintaining a pH value of liquid medicine.

13. The suspension of claim 12, wherein the pH regulator is selected from the group consisting of citric acid, hydrochloric acid, sodium hydroxide and pH buffer.

14. The suspension of claim 13, wherein the pH buffer is one selected from the group consisting of citric acid-sodium citrate, acetic acid-sodium acetate and sodium dihydrogen phosphate-disodium hydrogen phosphate.

15. The suspension of claim 1, wherein the osmotic pressure regulator is one selected from the group consisting of sodium chloride, potassium chloride, glucose, mannitol, xylitol and lactose.

* * * * *